United States Patent [19]
Beede et al.

[11] 4,335,158
[45] Jun. 15, 1982

[54] BANDAGE CARRYING ION-LEACHABLE CEMENT COMPOSITIONS

[75] Inventors: Charles H. Beede, East Brunswick; Richard N. Zirnite, Somerset, both of N.J.

[73] Assignee: Johnson & Johnson, New Brunswick, N.J.

[21] Appl. No.: 204,983

[22] Filed: Nov. 7, 1980

[51] Int. Cl.³ .............................................. A61F 5/04
[52] U.S. Cl. ........................................... 427/2; 128/90
[58] Field of Search ............... 427/2, 4; 128/90, 89 R

[56] References Cited

U.S. PATENT DOCUMENTS

| | | | |
|---|---|---|---|
| 4,005,706 | 2/1977 | Smith | 128/90 |
| 4,043,327 | 8/1977 | Potter | 128/90 |
| 4,108,169 | 8/1978 | Parker | 128/90 |

*Primary Examiner*—Sam Silverberg
*Attorney, Agent, or Firm*—Jason Lipow

[57] ABSTRACT

A method for producing a substrate carrying a cementitious composition is provided. The method involves dispersing a mixture of an ion-leachable, inorganic compound and a poly(carboxylic acid) in a liquid to form a coating mixture wherein the liquid is selected to be a non-aqueous, non-leachable liquid in which the poly(carboxylic acid) is substantially soluble. The coating mixture is then applied to the substrate.

9 Claims, No Drawings

BANDAGE CARRYING ION-LEACHABLE CEMENT COMPOSITIONS

BACKGROUND OF THE INVENTION

This invention relates to bandages carrying cement compositions comprising ion-leachable inorganic compounds preferably in the form of glasses. In particular, this invention relates to coating a suitable substrate with such cement compositions to produce an orthopedic bandage.

Ion-leachable inorganic compounds such as the oxides of aluminum, zinc, magnesium, and calcium have been intermixed with other components such as silica and formed into glasses which, when combined with such hydrogen-donating compounds as acids, will set up into a cementitious mass. The mechanisms for the reaction has been described by Alan D. Wilson, et al. (Journal of Dental Research, Volume 58, No. 3, at pps. 1065–1071, March 1979), and can be presented by the generic equation:

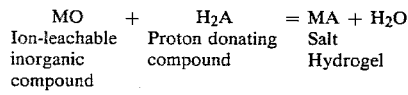

Cements utilizing this mechanism have generally taken the form of glass powders incorporating the ion-leachable inorganic. These are reacted with acid solutions such as aqueous, poly(carboxylic acid) solutions to form a salt hydrogel structure which sets up to a hard mass. Such cement-forming compositions have been suggested for use in application such as dental cements and for orthopedic purposes; i.e., casts and splints. For example, a fluoroaluminosilicate glass powder has been suggested for use as the ion-leachable component for dental cement as in British Pat. No. 1,316,129. Similarly, such a composition has been suggested for use in orthopedic surgery in U.S. Pat. Nos. 4,143,018 and 4,043,327.

Traditionally, the orthopedic practitioner is accustomed to being provided with a dry roll of bandaging material impregnated or coated with a cementitious composition, generally plaster of Paris. The practitioner then dips the roll into a bucket of water, wraps the bandage around the limb of the patient where, after a short time, the bandage sets to a rock-like hardness.

In attempting to emulate this cast-forming procedure and employ ion-leachable cement compositions such as have been used in the dental field, certain difficulties have been encountered. Firstly, the method employed by the dental practitioner cannot be readily translated to the orthopedic field. In dentistry, the cementitious composition is provided in two parts; the ionomer glass component and an aqueous solution of the poly(carboxylic acid) component. The dentist, requiring only small quantities of a cementitious mass at any given time, can easily mix these two parts just at the time of use without any great inconvenience. Unfortunately, this method is totally impractical for the orthopedist in that he requires large quantities of cementitious mixture at a given time and his difficulties are further compounded by the fact that he requires this cementitious material in the form of a wrapping for a limb.

In view of the above, it has been suggested that powderous forms of the ionomer glass, the poly(carboxylic acid) and any other additives such as accelerators, modifiers, deodorants, or the like, be intermixed and held in suspension in a non-aqueous non-reactive organic liquid. This suspension can then be coated onto a bandage substrate such as gauze and, when dried, will adhere to the substrate to produce a dry orthopedic bandage. The bandage can then be used in the same manner as those plaster of Paris bandages with which the orthopedist is most familiar; i.e., it may be dipped in water to become activated (begin the gelation reaction) and then wrapped around the limb of the patient and set into a rock-like cast. It has been variously suggested that such non-reactive organic liquids could be, for example, methyl ethyl ketone, methylene chloride, or cyclohexane (See U.S. Pat. No. 4,043,327, issued Aug. 23, 1977, to Potter, et al.; Dutch Specification No. 7604906, published Nov. 16, 1976, in the name of Smith and Nephew Research Ltd. and Pilkington Bros. Ltd.; South Africa Application No. 747391 published Nov. 15, 1974, in the name of National Research Development Corporation; and British Provisional Specification No. 55471, published in 1973).

While such prior art suggestions can be utilized and will produce a usable bandage, several drawbacks are encountered in an attempt to employ this method to the high speed production of commercially available quantities of orthopedic bandages. For example, it has been discovered that only a very limited amount of the solid material can be held suspended in the liquids suggested by the prior art. Accordingly, in order to provide a bandage carrying the requisite quantity of cementitious composition an impractically large quantity of the suspension must be deposited into the bandage substrate requiring, in turn, a considerable effort in both processing time and energy requirement to drive off the liquid and produce a dry bandage. Since these liquids are relatively expensive, a commensurability large amount in time and energy is required to recover and recycle the liquid driven off. Further, it has been discovered that while a limited quantity of the solid cementitious material can be induced into suspension in the suggested liquids, such suspensions are not stable and instead settle out after an impractically short period of time thus requiring that the coating suspension either be prepared immediately before use or else that elaborate stirring and agitation means be provided to keep the solids in suspension during the coating process.

Still further, it has been discovered that after the suspending liquid has been driven off, the solid materials do not cling readily to the bandage and instead dust off in obvious detriment to the entire process.

In view of the above drawbacks, an improved method for providing an orthopedic bandage with an ionomer cement composition is required.

SUMMARY OF THE INVENTION

In accordance with the teachings of this invention, a method is provided for coating a substrate with an ionomer cementitious composition of the kind comprising an ion-leachable inorganic compound and a poly(carboxylic acid) which does not suffer from the drawbacks associated with prior methods. In particular, a method is provided whereby large quantities of the cementitious composition may be coated onto the substrate in conjunction with comparatively small quantities of dispersing liquid. The coating dispersions of this invention are stable and may be stored for days at a time and then used without having to re-suspend the solids therein.

The solids in the resulting product cling tenaceously to the substrate without undue dusting.

In accordance with the teaching of this invention, the inorganic ion-leachable compound and the poly(carboxylic acid) are combined in non-aqueous, non-reactive liquid in which the poly(carboxylic acid) is substantially soluble. Specifically, the liquid chosen to be used is one in which the poly(carboxylic acid) is soluble at least to the extent of about ten, and preferably about twenty, parts by weight of the acid per 100 parts by weight of the liquid, at room temperature. Accordingly, the coating suspension consists of a solution of the acid and liquid is the dispersing or continuous phase in which the ion-leachable inorganic component, as well as any other solid additives employed, is suspended. It has been discovered that in marked contrast to prior suggested coating mixtures, solids contents of 60% or more are obtainable and can be held in essentially homogeneous dispersion for a period of days at a time without further agitation or processing. In this connection, it should be noted that as used herein, the term "solids contents" is meant to denote the weight of the originally solid material, including for example, the weight of the dissolved poly(carboxylic acid), as a percentage of the weight of the total coating dispersion.

In addition to the processing advantages accrued from the teachings of this invention, it has been further discovered that a uniquely advantageous product results after coating the bandage substrate and then driving off the prescribed liquid. Because the poly(carboxylic acid) was present in the coating dispersion in the dissolved form, the acid is precipitated onto the bandage in the form of an essentially continuous film which adheres to tenaciously such commonly used bandage substrates as woven or nonwoven fabrics. Moreover, the acid film acts as a matrix for retaining the dispersed solids; i.e., the ion-leachable inorganic components and any other additives employed. The resultant bandage is highly resistant to the dusting problem common to the prior suggested bandages.

In a preferred embodiment, the dispersing liquids of choice are selected from the group consisting of methanol, dioxane, tetrahydrofuran, 2-ethoxyethanol, 2-methoxyethanol and mixtures of these compounds.

DETAILED DESCRIPTION OF THE INVENTION

The invention comprises preparing a coating dispersion of an ion-leachable inorganic component, poly(carboxylic acid) and non-aqueous, non-reactive dispersing liquid in which the poly(carboxylic acid) is soluble to an appreciable extent.

The ion-leachable inorganic compounds are preferably introduced in the form of glass powders which have been formed from the oxides of alkali, alkaline earth, aluminum and zinc metals along with silica. As has been more fully discussed in a commonly assigned pending U.S. patent application filed on this same day and incorporated herein by reference, it is advantageous to provide such glass powder in as homogeneous a state as is possible and with a controlled and precise degree of crystallinity. In this aforementioned U.S. patent application, a method for realizing these criteria is described and basically comprises feeding shaped charged materials into an electric furnace, melting the materials to a molten mixture, blowing the molten mixture into thin glass fibers, and immediately quenching the fibers in a water bath. The quenched fibers are then dried and milled into the desired glass powder form.

The poly(carboxylic acid) may be one or more poly(acids) on their precursors and include polymers of monocarboxylic acids, monocarboxylic acid anhydrides, dicarboxylic acids and dicarboxylic acid anhydrides, as well as interpolymers of the above or interpolymers of the above and other ethenically unsaturated monomers. Examples of usable acids and precursors are poly(acrylic acid), itaconic-acrylic acid copolymers, itaconic acid polymer, poly(arylsulfonic acids), poly(methacrylic acid), ethylacrylate-acrylic acid copolymer, and the like. Also usable are a series of poly(methyl vinyl ether/maleic anhydride) copolymers sold by the GAF corporation under the trade name "Gantrez". All of these are available as finely divided solids which may be blended with the other ingredients.

In accordance with the teachings of this invention, a coating mixture is made by dispersing the ion-leachable inorganic and the poly(carboxylic acid) in a dispersing liquid selected to be non-reactive and in which the poly(carboxylic acid) will go into solution to the extent of at least 10 grams of poly(carboxylic acid) per 100 grams of dispersing liquid, when measured at room temperature. Preferably, the poly(carboxylic acid) is soluble to the extent of at least 20 gm/per 100 grams of dispersing liquid. It should be noted that by the term "non-reactive" it is meant a liquid which, when combined with the other ingredients of the cementitious composition, will not set up; i.e., begin the gelation reactions. Instead, this reaction will not occur until large excess quantities of water are introduced.

A substantial number of organic solvents may be employed as the dispersing liquid and, when chosen to have the properties described above, will produce coating mixtures which consist essentially of a dispersion of the ion-leachable inorganic suspended in a solution of the poly(carboxylic acid). By following the teachings herein, a large quantity of solids may be held in the dispersing liquid in an essentially homogeneous mixture. For example, the ion-leachable components and the poly(carboxylic acid) may make up 45% and even as much as 60% or more by weight of the coating mixture and still be stably dispersed by the dispersing liquid. Further, in addition to the above two components, other additives to the cementitious mixture may also be held in essentially homogeneous dispersion. For example, certain modifying agents such as those disclosed in our two U.S. patent applications, filed on this same day, may be held by the dispersing liquid. Generally, these are compounds provided to modify the rate of setting of the cementitious mixture when reacted with water. Examples of these are d,l-tartaric acid and certain water insoluble non-hydroxylic polycarboxylic aromatic compounds; e.g., terephthalic acid. Still other components may be provided in the coating mixture such as coloring agents, deodorizers, antimicrobial agents and the like.

While dispersing liquids having the herein prescribed properties will result in advantageous coating mixtures, it is preferred that the dispersing liquid be selected from the group consisting of methanol, dioxane, tetrahydrofuran, 2-ethoxyethanol, 2-methoxyethanol, and mixtures thereof. It has been discovered that these particular solvents produce coating mixtures having sufficient viscosities to enhance the stability of the dispersion.

It has further been discovered that by following the teachings of this invention, a unique dry bandage results. In contrast to prior methods in which the poly(- carboxylic acid) is held in particulate form by the dispensing liquid, in accordance with the teachings herein, the poly(carboxylic acid) is dissolved into the dispersing liquid. Accordingly, since the poly(carboxylic acid) is a film-forming polymer, upon drying a substrate coated with the coating mixture of this invention a substantially continuous film of the acid is laid down upon the surface of the substrate. Such a film has been found to cling tenaciously to such commonly used substrates such as gauze and, further, provides a matrix for holding the non-dissolved components of the cementitious composition; e.g., the ion-leachable component. The orthopedic bandage resulting from following the teachings of this invention, therefore, is less likely to dust or otherwise lose its cementitious composition prior to use.

The coating mixtures of this invention may be applied to essentially any of the commonly used substrates now employed in orthopedic bandages. These include both woven and nonwoven fabrics with gauze being most usually employed. Tightly woven gauze having a count of from 44×36 to loosely woven gauze having a count of 20×24 may be used. The weight of cementitious mixture deposited from the coating mixture onto the substitute may vary in accordance with the properties of the mixture and the use to which the bandage is put. Weights of 200 to 500 gms/yd$^2$ and preferably 250 to 400 gms/yd$^2$ are advantageously employed.

To illustrate the advantages of this invention, the following examples are given:

EXAMPLE 1

A powderous cementitious mixture of glass powder, polyacrylic acid and d,l-tartaric acid is prepared. The glass powder is one made in accordance with the process described in the above referred to co-pending patent application filed by Smyth on this day and chemically consists of 5.2 molar parts of $SiO_2$, 2.6 molar parts of Ca and 2.2 molar parts of ZnO. The poly(acrylic acid) has a molecular weight of 165,000. The d,l-tartaric acid is present to accelerate the setting time of the cementitious mixture in use as is disclosed in our co-pending patent application filed this day. The components are present in the weight ratio of 20 parts glass to 4.8 parts poly(acrylic acid) to 1.0 part d,l-tartaric acid. Seven grams of this powderous composition is dispersed in 10 grams of liquid methyl-ethylketone by stirring the powder into the liquid. The powder is observed to settle out of the liquid in less than one minute. When an attempt is made to coat a 32 by 28 count gauze substrate, the coating is uneven owing to the rapid settling and an unsatisfactory bandage results.

EXAMPLE 2

The procedure of Example 1 above is followed with the exception that perchlorethylene is substituted for the methyl ethyl ketone liquid. Once again the solids rapidly settle out although in this case the solids are held in dispersion long enough to coat the gauze substrate measuring about 24 by 3 inches fairly evenly with 130 g. of solids per square yard of gauze. The resulting bandage is dried in a steam cabinet and is found to dust to the extent that the major portion of solids coated onto the bandage falls off.

EXAMPLE 3

A series of cementitious powderous compositions are prepared consisting of glass, poly(acrylic acid) and modifying acid of this type and properties set out in Table 1 below. The glass chemically consists of 4 molar parts $SiO_2$, 2.5 molar parts $Al_2O_3$ and 3.5 molar parts CaO. In accordance with the teachings of this invention and in contrast with the prior examples, these compositions are dispersed in liquids in which the quantity of poly(acrylic acid) employed is essentially totally dissolved. In each case, a coating mixture results which is highly stable and in fact is usable many days later. Each of the samples set out in Table 1 is coated onto a 32 by 28 count gauze substrate to the weights shown in the Table and dried in a steam cabinet to form a coated orthopedic bandage. The solids are found to adhere tenaciously to the gauze. Three strips of each of the bandages produced, measuring 1.5 inches by 12 inches, are dipped in a pail of water at 30° C. for 20 seconds. Each strip is then wrapped around a 0.5 inch diameter steel rod covered with wax paper. The plies are smoothed as the wrapping progresses in a manner very similar to the technique used in wrapping plaster casting tapes. The casts are cured at 70° F. (21° C.) for three days. The deflection strength is then measured by using an Instron Tester to determine the average value for the force per unit weight of cast required to deflect the hollow cylinder by reducing the inside diameter by 15%. This value is recorded below in Table 1 as the deflection strength. As a control, plaster of Paris casts are made and tested in the same manner. These have deflection strength of from about 1 to 3 lbs./gm.

| | | Cement Composition | | | | Dispersion | | | |
|---|---|---|---|---|---|---|---|---|---|
| | | Poly (Acrylic Acid) | | (Modifying Acid) | | Dispersing | % | Coating Weight | Deflection Strength |
| Sample | Glass Parts | Mole. Wt. | Parts | Type | Parts | Liquid | Solids | Strength | lbs/gm. |
| 1 | 2 | 86,500 | 0.84 | d,l-tartaric | 0.16 | Tetrahydrofuran | 50 | 9.3 | 17.5 |
| 2 | 2 | 86,500 | 0.84 | d,l-tartaric | 0.16 | Dioxane | 50 | 10.9 | 14.9 |
| 3 | 2 | 164,700 | 0.84 | d,l-tartaric | 0.16 | 2-Ethoxyethanol | 50 | 9.5 | 16.5 |
| 4 | 2 | 164,700 | 0.84 | d,l-tartaric | 0.16 | Methanol | 50 | 8.8 | 18.3 |
| 5 | 2 | 75,800 | 0.84 | d,l-tartaric | 0.16 | Methanol/2-ethoxyethanol (1) | 60 | 12.2 | 16.1 |
| 6 | 2 | 75,800 | 0.84 | Terephthalic | 0.16 | Methanol/2-ethoxyethanol (1) | 60 | 13.3 | 12.4 |
| 7 | 2 | 86,500 | 0.84 | d,l-tartaric | 0.16 | Methanol/2-ethoxyethanol (1) | 60 | 12.0 | 17.7 |
| 8 | 2 | 86,500 | 0.84 | Terephthalic | 0.16 | Methanol/2-ethoxyethanol (1) | 60 | 12.0 | 14.9 |
| 9 | 2 | 575,800 | 0.84 | d,l-tartaric | 0.16 | Methanol/2-ethoxyethanol (1) | 56 | 12.0 | 18.1 |
| 10 | 3 | 414,000 | 0.84 | Terephthalic | 0.16 | Methanol/2-Methoxyethanol (1) | 60 | 12.2 | 3.2 |
| 11 | 3 | 414,000 | 0.84 | Terephthalic | 0.16 | Methanol/2- | | | |

-continued

| | | Cement Composition | | | | Dispersion | | | |
|---|---|---|---|---|---|---|---|---|---|
| Sample | Glass Parts | Poly (Acrylic Acid) Mole. Wt. | Parts | (Modifying Acid) Type | Parts | Dispersing Liquid | % Solids | Coating Weight Strength | Deflection Strength lbs/gm. |
| 12 | 3 | 414,000 | 0.84 | Terephthalic | 0.16 | Methoxyethanol (1) | 62 | 9.6 | 17.4 |
| 13 | 3 | 414,000 | 0.84 | Terephthalic | 0.16 | Methylethyl Ketone (2) | 50 | 9.7 | 10.4 |
|    |   |         |      |              |      | Methylethyl Ketone (2) | 50 | 10.6 | 13.3 |

(1) 1:1, by weight
(2) with 2% by weight hydroxypropyl cellulose

What is claimed is:

1. A method for producing a substrate carrying a cementitious composition comprising:

dispersing a mixture comprising an ion-leachable inorganic component and a poly(carboxylic acid) in a liquid to form a coating mixture, said liquid comprising a non-aqueous, non-reactive liquid in which said poly(carboxylic acid) is substantially soluble; said liquid being selected from the group consisting of methanol, dioxane, tetrahydrofuran, 2-ethoxyethanol, 2-methoxyethanol, and mixtures thereof; and applying said coating mixture to said substrate.

2. The method of claim 1 wherein said coating mixture is chosen to be one in which the poly(carboxylic acid) is soluble to at least the extent of about ten parts by weight of the poly(carboxylic acid) per 100 parts by weight of the liquid, at room temperature.

3. The method of claim 2 wherein said liquid is one in which the poly(carboxylic acid) is soluble to at least the extent of about 20 parts by weight of the poly(carboxylic acid) per 100 parts by weight of the liquid, at room temperature.

4. The method of claim 1 wherein said mixture of ion-leachable component and poly(carboxylic acid) comprise at least 45% by weight of said coating mixture.

5. The method of claim 1 wherein said substrate is gauze.

6. The method of claim 1 wherein said poly(carboxylic acid) is selected from the group consisting of the polymers and interpolymers of monocarboxylic acids, monocarboxylic acid anhydrides, dicarboxylic acids, and dicarboxylic acid anhydrides.

7. The method of claim 6 wherein said poly(carboxylic acid) is poly(acrylic acid).

8. The method of claim 1 wherein said ion-leachable component is a glass powder.

9. The method of claim 8 wherein said glass powder is formed from mixtures of silica and oxides of metals selected from the group consisting of alkali, alkaline earth, aluminum and zinc metals.

* * * * *